(12) United States Patent
Knifton et al.

(10) Patent No.: US 7,276,634 B2
(45) Date of Patent: Oct. 2, 2007

(54) REDUCTION OF THE VISCOSITY OF REACTIVE HEAVY BYPRODUCTS DURING THE PRODUCTION OF 1,3-PROPANEDIOL

(75) Inventors: John Frederick Knifton, Houston, TX (US); Talmadge Gail James, Houston, TX (US); Paul Richard Weider, Houston, TX (US); Joseph Broun Powell, Houston, TX (US); Edward Lewis Nielsen, Houston, TX (US); Glenn Charles Komplin, Houston, TX (US)

(73) Assignee: Shell Oil Company, Houston, TX (US)

( * ) Notice: Subject to any disclaimer, the term of this patent is extended or adjusted under 35 U.S.C. 154(b) by 662 days.

(21) Appl. No.: 10/676,682

(22) Filed: Oct. 1, 2003

(65) Prior Publication Data

US 2005/0043570 A1 Feb. 24, 2005

Related U.S. Application Data

(60) Provisional application No. 60/415,676, filed on Oct. 3, 2002.

(51) Int. Cl.
C07C 27/10 (2006.01)
(52) U.S. Cl. ..................................... 568/700
(58) Field of Classification Search ............... 568/682, 568/868
See application file for complete search history.

(56) References Cited

U.S. PATENT DOCUMENTS

| | | | | |
|---|---|---|---|---|
| 3,511,880 A | | 5/1970 | Booth ......................... 260/604 |
| 3,630,753 A | * | 12/1971 | Melnychyn et al. ........ 530/378 |
| 4,105,466 A | * | 8/1978 | Kunkle et al. .............. 106/486 |
| 4,111,202 A | * | 9/1978 | Theeuwes ................. 604/892.1 |
| 4,242,284 A | | 12/1980 | Harris et al. ................ 568/454 |
| 4,861,918 A | | 8/1989 | Miller et al. ................ 568/454 |
| 4,873,378 A | | 10/1989 | Murphy et al. ............. 568/867 |
| 4,873,379 A | | 10/1989 | Murphy ...................... 568/867 |
| 5,015,789 A | | 5/1991 | Arntz et al. ................. 568/862 |
| 5,030,766 A | | 7/1991 | Briggs et al. ............... 568/496 |
| 5,053,562 A | | 10/1991 | Tau ............................. 568/867 |
| 5,171,898 A | | 12/1992 | Arntz et al. ................. 568/862 |
| 5,210,318 A | | 5/1993 | Briggs et al. ............... 568/496 |
| 5,256,827 A | | 10/1993 | Slaugh et al. ............... 568/454 |
| 5,276,201 A | | 1/1994 | Haas et al. .................. 568/491 |
| 5,304,686 A | | 4/1994 | Slaugh et al. ............... 568/496 |
| 5,304,691 A | | 4/1994 | Arhancet et al. ........... 568/867 |
| 5,334,778 A | | 8/1994 | Haas et al. .................. 568/862 |
| 5,364,987 A | | 11/1994 | Haas et al. .................. 568/866 |
| 5,426,249 A | | 6/1995 | Haas et al. .................. 568/862 |
| 5,744,649 A | | 4/1998 | Bryant et al. ............... 568/454 |
| 5,871,637 A | * | 2/1999 | Brons ......................... 208/283 |
| 5,904,839 A | * | 5/1999 | Brons ......................... 208/226 |
| 6,642,185 B2 | * | 11/2003 | Crews ......................... 507/273 |
| 6,988,550 B2 | * | 1/2006 | Bragg et al. ................ 166/275 |
| 2003/0236422 A1 | * | 12/2003 | Daniels ........................ 554/8 |
| 2005/0043570 A1 | * | 2/2005 | Knifton et al. ............. 568/868 |

FOREIGN PATENT DOCUMENTS

WO WO 97/16250 5/1997

OTHER PUBLICATIONS

"Properties of the Principal Fats, Fatty Oils, Waxes, Fatty Acids and Their Salts," by M. P. Doss, The Texas Company, 1952.
Rodds' Chemistry of Carbon Compounds, p. 87.
"β-Hydroxypropionic Acid," Organic Synthesis, Collective, vol. 1, 2nd Edition, p. 321.
"Surface-Active Derivatives, Soaps, and Detergents," by W. M. Lynfield.
"Complex Formation between Carboxylic Acids and Divalent Metal Cations," by R. Keith Cannan and Andre Kibrick, J. Amer. Chem. Soc., 60, (1938) pp. 2314-2320.
International Search Report of Mar. 2, 2004.
U.S. Appl. No. 08/550,589, filed Oct. 31, 1995, Lam et al.

* cited by examiner

*Primary Examiner*—Yvonne Eyler
*Assistant Examiner*—M Louisa Lao

(57) ABSTRACT

The present invention is an improvement upon the process for the production of 1,3-propanediol wherein an aqueous solution of 3-hydroxy propanal is formed, catalyst, if any, used in said formation is removed from the solution, sodium hydroxide is added to the solution to neutralize any acid therein such that the pH is at least about 5, the neutralized aqueous solution is subjected to hydrogenation to produce a crude 1,3-propanediol mixture which is distilled to produce 1,3-propanediol, water, and reactive heavy components. The improvement on this process comprises replacing the sodium hydroxide with a hydroxide selected from the group consisting of ammonium hydroxide, alkali metal hydroxides other than sodium hydroxide, and alkaline earth metal hydroxides to reduce the viscosity of the reactive heavy components.

6 Claims, No Drawings

REDUCTION OF THE VISCOSITY OF REACTIVE HEAVY BYPRODUCTS DURING THE PRODUCTION OF 1,3-PROPANEDIOL

This application claims the benefit of U.S. Provisional Application No. 60/415,676 filed Oct. 3, 2002, the entire disclosure of which is hereby incorporated by reference.

FIELD OF THE INVENTION

This invention relates to a process for the production of 1,3-propanediol (PDO) wherein an aqueous solution of 3-hydroxy propanal is formed, catalyst used in said formation is removed from the solution, hydroxide is added to the solution to neutralize any acid therein, and the neutralized aqueous solution is hydrogenated to produce a PDO mixture which is distilled to produce purified PDO.

BACKGROUND OF THE INVENTION

Several companies have developed technology for the manufacture of PDO starting with ethylene oxide as the main raw material. The ethylene oxide is reacted with synthesis gas (syngas), a mixture of carbon monoxide and hydrogen, which may be obtained by steam reforming of natural gas or partial oxidation of hydrocarbons. The idealized reaction of ethylene oxide (EO) with syngas to yield PDO is shown below:

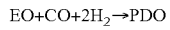

U.S. Pat. Nos. 4,873,378, 4,873,379, and 5,053,562 from Hoechst Celanese describe a single step reaction using 2:1 (molar) syngas at 110 to 120° C. and about 1000 psig to give 65 to 78 mole percent yield of PDO and precursors thereof. The catalyst system used consisted of rhodium, various phosphines, and various acids and water as promoters.

U.S. Pat. Nos. 5,030,766 and 5,210,318 to Union Carbide describe the reaction of EO with syngas in the presence of rhodium-containing catalysts. At 110° C. and 1000 psig of 2:1 molar syngas, a selectivity of up to 47 mole percent was achieved but the combined rate of formation of PDO and 3-hydroxy propanal was quite low at 0.05 to 0.07 moles per liter per hour. Better results were achieved by increasing the ratio of phosphoric acid promoter to rhodium catalyst.

U.S. Pat. Nos. 5,256,827, 5,304,686, and 5,304,691 to Shell Oil described PDO production from EO and syngas utilizing tertiary phosphine-complexed cobalt carbonyl catalysts. Reaction conditions of 90 to 105° C. and 1400 to 1500 psig of syngas (1:1 molar ratio) for three hours produced selectivities in the range of 85 to 90 mole percent and the EO conversion was in the range of 21 to 34 percent.

SUMMARY OF THE INVENTION

The present invention is an improvement upon the process for the production of 1,3-propanediol wherein an aqueous solution of 3-hydroxy propanal is formed, catalyst, if any, used in said formation is removed from the solution, sodium hydroxide is added to the solution to neutralize any acid therein such that the pH is at least about 5, and the neutralized aqueous solution is subjected to hydrogenation to produce a crude 1,3-propanediol mixture which is distilled to produce 1,3-propanediol, water, and reactive heavy components. The improvement on this process comprises replacing the sodium hydroxide with a hydroxide selected from the group consisting of ammonium hydroxide, alkali metal hydroxides other than sodium hydroxide, and alkaline earth metal hydroxides to reduce the viscosity of the reactive heavy components.

DETAILED DESCRIPTION OF THE INVENTION

The 3-hydroxy propanal (HPA) aqueous solution which is the starting material of the present invention, can be produced by a number of different processes. The aforementioned U.S. Pat. Nos. 4,873,378, 4,873,379, 5,053,562, 5,030,766, 5,210,318, 5,256,827, 5,304,686, and 5,304,691, all of which are herein incorporated by reference, describe different methods for producing aqueous solutions of HPA. HPA can also be produced by hydration of acrolein in the presence of acidic catalysts. Processes for accomplishing this result are described in U.S. Pat. Nos. 5,426,249, 5,015,789, 5,171,898, 5,276,201, 5,334,778, and 5,364,987, all of which are herein incorporated by reference.

A preferred method for carrying out the entire process of the present invention is described as follows. EO is preferably hydroformylated in a reactor such as a bubble column or agitated tank at about 200 to about 5000 psi (about 1380 to about 34,500 kPa) of syngas having a ratio of hydrogen to carbon monoxide of about 1:5 to about 25:1, about 50 to about 110° C., in the presence of a cobalt catalyst at a concentration of about 0.01 to about 1.0 weight percent (% wt) of the total reaction mixture.

The hydroformylation reaction effluent is preferably extracted with a small amount of water at water-solvent ratios ranging from about 2:1 to about 1:20 at about 5 to about 55° C. under an atmosphere of about 50 to about 200 psi (about 350 to about 1380 kPa) carbon monoxide. The solvent layer containing more than about 90 percent of the cobalt catalyst in active form is recycled back to the hydroformylation reactor. The HPA concentrates in the water layer at a concentration of about 10 to about 45 weight percent of the total water layer.

The cobalt is preferably removed from this aqueous solution of HPA by first oxidizing the cobalt and then extracting it utilizing an acid ion exchange resin. The ion exchange resin may be a weak or strong acid ion exchange resin.

The aqueous solution from which the cobalt has been removed contains organic acid which must be neutralized because the acidity cannot be handled in downstream carbon steel equipment and because of potential degradation of catalyst downstream. The aqueous HPA solution is neutralized such that the pH of the solution is at least about 5. Preferably, the pH is in the range of about 5 to about 6 because the condensation of 3-hydroxy propanal is strongly catalyzed by base and operation within this range will reduce undesirable byproducts. In order to neutralize the acid in the solution as specified, the hydroxides of this invention preferably are added to the solution as an aqueous solution of about 5 to about 50% hydroxide by weight of the total solution. The amount of hydroxide used relative to the amount of 1,3-propanediol made may be from about 0.05 to about 5% by weight basis 1,3-propanediol but could be as much as 10% by weight. It probably would not be economical to add more than 10% by weight of hydroxide and typically, the range may be from 0.2 to 2% by weight.

In order to achieve the advantages of the present invention, the base or caustic which is used to neutralize the HPA aqueous solution is a hydroxide selected from the group consisting of ammonium hydroxide, alkali metal hydroxides other than sodium hydroxide, and alkaline earth metal hydroxides. When any one of these hydroxides is used in this process, the viscosity of the heavy ends stream (reactive heavy components stream from the bottom of the distillation column) produced during the distillation of the crude PDO mixture is generally low enough such that the heavy ends can be handled easily, the heavy ends stream can generally have a PDO concentration of about 30 percent by weight or less, and it generally is possible to recover PDO from the reactive heavy components. Specific preferred alkali metal and alkaline earth metal hydroxides include potassium hydroxide, lithium hydroxide, calcium hydroxide, barium hydroxide, cesium hydroxide, rubidium hydroxide, and strontium hydroxide. The most preferred hydroxides for use herein are potassium hydroxide, calcium hydroxide, barium hydroxide, and ammonium hydroxide. Potassium hydroxide is the most highly preferred hydroxide for use in this invention.

While not wishing to be bound by any theory, we believe the reactive heavy components comprise acetals of PDO/HPA, 3-hydroxypropionic acid, other carboxylic acids, and derivatives thereof. The materials, especially carboxylic acids, form viscous solutions in PDO with sodium hydroxide, probably because of the formation of gel networks. However, the solutions of the hydroxides of this invention are much less viscous, probably because of a breakup of said networks.

When sodium hydroxide is used, the reactive heavy components have a very high viscosity, i.e., on the order of about 5000 $mm^2/s$ (millimeters squared per second) at 40° C. This is because the nature of sodium salts in PDO is that they are very viscous. In fact, they are almost gels. The salts of the hydroxides of the present invention in PDO are much less viscous, i.e., preferably on the order of about 40 $mm^2/s$ or less at 40° C., usually about 100 $mm^2/s$ or less at 40° C. When sodium hydroxide is used, the distillation must be carried out such that the reactive heavy components stream contains from about 55 to about 70 weight percent of PDO or else the entire stream is too viscous to be distilled in conventional equipment. This PDO is lost because it is too expensive to distill out of the reactive heavy components stream and, even if the PDO was distilled out, it would leave a nasty sticky solid in the distillation column.

After neutralization of the aqueous solution of 3-hydroxy propanal, the aqueous solution is hydrogenated. This may be carried out by hydrogenation over a fixed bed of supported nickel catalyst at about 100 to about 2000 psi (about 690 to about 13,800 kPa) of hydrogen. Initial hydrogenation is generally conducted at about 40° C. and the temperature is increased to about 175° C. to encourage the reaction of reactive heavy components back to PDO. Finally, water and entrained light solvent and volatile impurities are distilled from the PDO and the reactive heavy components are also separated during distillation as the bottoms stream. These reactive heavy components are treated as described above.

The viscosity of the reactive heavy component stream produced in the distillation of the crude PDO is lowered by a factor of about 100 and more when the present invention is followed as opposed to the prior practice of using sodium hydroxide. This gives great process advantages in terms of handling the disposal and/or treatment and/or recycle and/or separation of PDO from these reactive heavy components. Also, the amount of residual PDO in the distillation column bottoms stream can be significantly reduced, resulting in improved economics.

EXAMPLES

Example 1

To 50 gm of PDO plant bottoms 1751B (containing reactive heavy components; sodium content 1.55% wt) was added 30 gm of Dowex® 50WX4-100, strongly acidic, ion exchange resin, 50-100 mesh, and the mixture stirred, under a nitrogen blanket, over the weekend. A sample of the supernatent liquid showed a sodium content of <0.005% wt.

The liquid fraction (24286-13-3) was recovered by filtration, and the filtrate divided into 10 gm portions.

One 10 gm portion of filtrate was treated with a solution of 0.27 gm of sodium hydroxide (NaOH) in distilled water (2.5 gm), and the new mix was rotary evaporated under vacuum (1 torr-0.133 kPa) at 40° C. The residual 5 cc of red liquid (24286-15-2) was judged to be very viscous.

A second 10 portion of filtrate was treated with a solution of 0.22 gm of potassium hydroxide (KOH) in distilled water (2.5 gm) and also rotary evaporated at 1 torr (0.133 kPa) and 40° C. The residual 5 cc of red liquid (24286-15-3) was judged to be a non-viscous liquid.

Example 2

Following the procedures of Example 1, 200 gm of PDO distillation bottoms 1751B was treated with 120 gm of Dowex® 50WX4-100 resin and the mixture was stirred under a nitrogen blanket to give a supernatent liquid containing sodium at <0.005% wt. The resin was removed by filtration and the filtrate (24286-19-1) divided into 60 gm portions.

One 60 gm portion was treated with a solution of 1.62 gm of sodium hydroxide in water (4.5 gm) and the new mix was evaporated at 1 torr (0.133 kPa) and 40° C. The residual reddish liquid (24286-19-2) was found to have a kinetic viscosity of 5686 $mm^2/s$ at 40° C.

A second 60 gm portion of filtrate was treated with a solution of 1.32 gm of KOH in water (4.5 gm) and the mix was evaporated at 1 torr (0.133 kPa) and 40° C. The residual red liquid (24286-19-3) was found to have a kinematic viscosity of 54 $mm^2/s$ at 40° C.

Example 3

Following the procedures of Examples 1 and 2, 200 gm of PDO distillation bottoms 1751B was treated with 120 gm of Dowex® 50WX4-100 resin to remove all sodium ions and the resin was removed by filtration. The new filtrate was #24286-21-1.

A 60 gm portion of the filtrate was treated with 2.64 gm of KOH in water (3.0 gm) and the mix evaporated at 1 torr (0.133 kPa) and 40° C. The residual red liquid (24286-21-2) had a kinematic viscosity of 43 $mm^2/s$ at 40° C.

A second 60 gm portion was treated with 0.66 gm of KOH in water (1.5 gm) and the mix was evaporated. Here the residual red liquid (24286-21-3) had a kinematic viscosity of 42 $mm^2/s$ at 40° C.

Example 4

Following the procedures of Examples 1-3, a 300 gm sample of PDO plant bottoms 1751B was treated with 120 gm of Dowex® 50WX4-100 resin to remove all sodium ions and the remaining resin was removed by filtration. The filtrate # was 24286-25-1.

A 60 gm portion of the filtrate was treated with 3.2 gm of lithium hydroxide in water 40 gm and the mix was rotary evaporated. The residual liquid (24286-25-2, 42.4 gm) had a viscosity of 914 mm$^2$/s at 40° C. and 28 mm$^2$/s at 100° C.

A second 60 gm portion was treated with 1.7 gm of calcium hydroxide in water (20 gm). The residue (24286-25-3, 43.0 gm) after evaporation had a kinematic viscosity of 88 mm$^2$/s at 40° C. and 11 mm$^2$/s at 100° C.

A third sample was treated with 1.2 gm of barium hydroxide in water (20 gm). The residue (24286-25-4, 39.2 gm) had a kinematic viscosity of 47 mm$^2$/s at 40° C. and 5.5 mm$^2$/s at 100° C.

Example 5

Since ammonium and potassium ions are of similar size, it was of interest to us to determine if neutralization of PDO bottoms fractions with ammonia, rather than alkali metal ions, could substantially lower the bottoms viscosity and thereby ease the processability and fluidity of these streams. We have conducted three sets of side-by-side experiments using as starting materials:

PDO bottoms 1751B, comprising ca. 65% PDO

PDO distillation bottoms #882246 ca. 40% wt. PDO

Samples of #882246 that were further fractionally distilled under vacuum to recover the remaining PDO; numbered 24286-29/35 bottoms In each case typical samples were neutralized with Dowex® 50WX4-100 acid resin (to remove all Na ions) then the liquid filtrate was back treated with the equivalent amount of ammonia—as ca. 28% wt. ammonium hydroxide solution in water. After stripping to remove added water, the residual liquids were submitted for viscosity measurements. The data tabulated below include, for comparison, our earlier reported viscosity measurements (in mm$^2$/s) for the same three sets of PDO Bottoms samples back-treated with potassium and sodium ions.

| Viscosity (in mm$^2$/s) at: | 40° C. | 100° C. |
|---|---|---|
| For PDO Distillation Bottoms #882246 | | |
| Na ions | Very viscous | >97,000 |
| K ions | 73.1 | 8.2 |
| NH$_4$ ions | 52.8 | 6.7 |
| For PDO Bottoms 3882246 Further Distilled to Remove All PDO Samples 24286-29/-35 | | |
| Na ions | Crystals | — |
| K ions | 50.9 | 6.1 |
| NH$_4$ ions | 91.4 | 11.1 |

-continued

| Viscosity (in mm$^2$/s) at: | 40° C. | 100° C. |
|---|---|---|
| For PDO Bottoms 1751B | | |
| Na ions | 5686 | — |
| K ions | 69.5 | 8.0 |
| NH$_4$ ions | 45.1 | 7.0 |
| 2 × NH$_4$ ions | 48.2 | 7.0 |

Clearly ammonia treatment of these various bottoms samples leads to a substantial reduction in viscosity in all exchanged materials as compared to sodium hydroxide solutions.

We claim:

1. In a process for the production of 1,3-propanediol wherein an aqueous solution of 3-hydroxy propanal is formed, catalyst, if any, used in said formation is removed from the solution, sodium hydroxide is added to the solution to neutralize acid therein such that the pH is at least about 5, the neutralized aqueous solution is subjected to hydrogenation to produce a crude 1,3-propanediol mixture which is distilled to produce 1,3-propanediol, water, and reactive heavy components, the improvement which comprises replacing the sodium hydroxide with a hydroxide selected from the group consisting of ammonium hydroxide, potassium hydroxide, lithium hydroxide, and calcium hydroxide to reduce the viscosity of the reactive heavy components.

2. The process of claim 1 wherein the pH is in the range of about 5 to about 6.

3. The process of claim 1 wherein the hydroxide which replaces the sodium hydroxide is potassium hydroxide.

4. A reactive heavy components stream having a viscosity of less than about 100 mm$^2$/s at 40° C., said stream formed by forming an aqueous solution of 3-hydroxy propanal, removing any catalyst used from the solution, adding to the solution a hydroxide selected from the group consisting of ammonium hydroxide, potassium hydroxide, lithium hydroxide, and calcium hydroxide to neutralize acid therein such that the pH is at least about 5, subjecting the neutralized aqueous solution to hydrogenation to produce a crude 1,3-propane diol mixture, and distilling said crude mixture to produce 1,3-propane diol, water, and the reactive heavy components stream.

5. The reactive heavy component stream of claim 4 wherein the pH is in the range of about 5 to about 6.

6. The reactive heavy component stream of claim 1 wherein the hydroxide which replaces the sodium hydroxide is potassium hydroxide.

* * * * *